US010420948B2

(12) United States Patent
Masoud et al.

(10) Patent No.: US 10,420,948 B2
(45) Date of Patent: Sep. 24, 2019

(54) IMPLANTABLE MEDICAL DEVICE WITH VARIABLE DATA RETRANSMISSION CHARACTERISTICS BASED UPON DATA TYPE

(75) Inventors: Javaid Masoud, Shoreview, MN (US); Charles H. Dudding, Lino Lakes, MN (US); Robert A. Patrias, Le Sueur, MN (US)

(73) Assignee: Medtronic, Inc., Minneapolis, MN (US)

( * ) Notice: Subject to any disclaimer, the term of this patent is extended or adjusted under 35 U.S.C. 154(b) by 2464 days.

(21) Appl. No.: 11/554,245

(22) Filed: Oct. 30, 2006

(65) Prior Publication Data

US 2008/0103551 A1 May 1, 2008

(51) Int. Cl.
*A61N 1/06* (2006.01)
*A61N 1/372* (2006.01)

(52) U.S. Cl.
CPC ..... *A61N 1/37252* (2013.01); *A61N 1/37276* (2013.01)

(58) Field of Classification Search
CPC ............ A61N 1/37276; A61N 1/37252; A61N 1/37223
USPC ................................................ 607/2, 59, 116
See application file for complete search history.

(56) References Cited

U.S. PATENT DOCUMENTS

| 5,476,488 | A | 12/1995 | Morgan et al. |
| 5,562,713 | A | 10/1996 | Silvian |
| 5,683,432 | A | 11/1997 | Goedeke et al. |
| 5,748,103 | A | 5/1998 | Flach et al. |
| 5,752,976 | A | 5/1998 | Duffin et al. |
| 5,807,336 | A | 9/1998 | Russo et al. |
| 5,843,139 | A | 12/1998 | Goedeke et al. |
| 5,944,745 | A | 8/1999 | Rueter |
| 6,073,050 | A | 6/2000 | Griffith |
| 6,201,993 | B1 | 3/2001 | Kruse et al. |
| 6,516,227 | B1 * | 2/2003 | Meadows ............ A61N 1/0553 607/117 |
| 6,561,975 | B1 * | 5/2003 | Pool et al. ..................... 600/300 |
| 6,766,198 | B1 | 6/2004 | Snell |
| 7,065,409 | B2 | 6/2006 | Mazar |
| 7,069,086 | B2 | 6/2006 | Arx |
| 7,502,594 | B2 | 3/2009 | Ginggen et al. |

(Continued)

FOREIGN PATENT DOCUMENTS

| EP | 0607638 A | 7/1994 |
| WO | WO0197907 A | 12/2001 |
| WO | 2005/061048 A1 | 7/2005 |

OTHER PUBLICATIONS

International Search Report, PCT/US2007/081576, dated Oct. 22, 2008, 7 Pages.

*Primary Examiner* — Michael J D Abreu

(57) ABSTRACT

An implantable medical device ("IMD") as described herein includes an adjustable data retransmission scheme, which controls the manner in which data is retransmitted by the IMD. The retransmission feature can be adjusted in a dynamic manner based upon the type, context, or meaning of the telemetry data transmitted by the IMD. The IMD may process contextual meaning information that influences its data retransmission configuration. Such adjustability enables the IMD to satisfy minimum telemetry requirements in a manner that does not waste power, thus extending the IMD battery life.

22 Claims, 7 Drawing Sheets

(56) References Cited

U.S. PATENT DOCUMENTS

| | | | |
|---|---|---|---|
| 2002/0072783 A1* | 6/2002 | Goedeke | A61B 5/0031 607/60 |
| 2003/0199939 A1 | 10/2003 | Schmitt et al. | |
| 2004/0030260 A1 | 2/2004 | Von Arx | |
| 2005/0137480 A1* | 6/2005 | Alt | A61B 5/0031 600/508 |
| 2005/0197680 A1 | 9/2005 | Delmain et al. | |
| 2005/0251579 A1* | 11/2005 | Ngo et al. | 709/234 |
| 2005/0283208 A1 | 12/2005 | Von Arx et al. | |
| 2005/0288738 A1 | 12/2005 | Bange et al. | |
| 2006/0020301 A1 | 1/2006 | Hanson et al. | |
| 2006/0030901 A1 | 2/2006 | Quiles et al. | |
| 2007/0123946 A1 | 5/2007 | Masoud | |
| 2007/0255318 A1 | 11/2007 | Dudding et al. | |
| 2008/0015656 A1* | 1/2008 | Bange et al. | 607/32 |
| 2008/0027501 A1 | 1/2008 | Haubrich et al. | |

* cited by examiner

IMPLANTABLE MEDICAL DEVICE WITH VARIABLE DATA RETRANSMISSION CHARACTERISTICS BASED UPON DATA TYPE

TECHNICAL FIELD

The present invention generally relates to implantable medical devices ("IMDs"). More particularly, the present invention relates to data transmission from IMDs.

BACKGROUND

IMDs provide therapies to patients suffering from a variety of conditions. Examples of cardial IMDs are pacemakers and implantable cardioverter-defibrillators ("ICDs"). Such IMDs generally monitor the electrical activity of the heart and provide electrical stimulation to one or more of the heart chambers when necessary. For example, pacemakers are designed to sense arrhythmias, e.g., disturbances in heart rhythm, and, in turn, provide appropriate electrical stimulation pulses at a controlled rate to selected chambers of the heart in order to correct the arrhythmias and restore the proper heart rhythm. The types of arrhythmias that may be detected and corrected by pacemakers include bradycardias (slow heart rates) and certain tachycardias (fast heart rates).

ICDs also detect arrhythmias and provide appropriate electrical stimulation pulses to selected chambers of the heart to correct the abnormal heart rate. In contrast to pacemakers, however, an ICD can also provide pulses that are much stronger and less frequent, where such pulses are generally designed to correct fibrillation, which is a rapid, unsynchronized quivering of one or more heart chambers, and severe tachycardias, during which the heartbeats are very fast but coordinated. To correct such arrhythmias, ICDs deliver low, moderate, or high-energy therapy pulses to the heart.

Generally, IMDs are equipped with on-board memory in which data can be stored for later retrieval and analysis via telemetry. Typically, the telemetered signals can provide patient physiologic and cardiac information. This information is generally recorded on a per heartbeat, binned average basis, or derived basis, and involve, for example, atrial electrical activity, ventricular electrical activity, minute ventilation, patient activity score, cardiac output score, mixed venous oxygen score, cardiovascular pressure measures, time of day, and any interventions and the relative success of such interventions. Telemetered signals can also be stored in a broader class of monitors and therapeutic devices for other areas of medicine, including metabolism, endocrinology, hematology, neurology, muscular disorders, gastroenterology, urology, ophthalmology, otolaryngology, orthopedics, and similar medical subspecialties.

Generally, upon detecting arrhythmias and, when necessary, providing corresponding therapies to correct such arrhythmias, IMDs store the data over a set period of time (usually before, during, and after the occurrence of such arrhythmic event). Current practice in the art involves the use of an external communication unit, e.g., an external programmer, for non-invasive communication with IMDs via uplink and downlink communication channels associated with the communication device. In accordance with conventional medical device programming systems, a programming head can be used for facilitating one or two-way communication between IMDs and the external communication device. In many known IMD systems, the programming head can be positioned on the patient's body over the IMD such that the programming head can send wireless signals to, and receive wireless signals from, the IMD.

Implementation and operation of most, if not all, RF communication systems for IMDs and external communication devices involves a balancing or compromising of certain countervailing considerations, relating to such interrelated operational parameters as data transmission rate, transmission range, IMD power consumption and battery life, among numerous others. Such operational parameters are often interrelated in the sense that the adjustment of one operating parameter may permit or require the adjustment of one or more other operating parameters even while predetermined system performance goals and/or requirements continue to be met and predetermined limitations imposed upon operational parameter adjustment are adhered to. For example, to meet a minimum transmission range, the transmitter output power of an IMD must provide telemetry signals having sufficient energy.

Conventional IMDs may employ data retransmission techniques for redundancy and/or to ensure that data is successfully transmitted under poor channel conditions. Some IMDs employ a default retransmission scheme where each transmitted packet or frame is always retransmitted at least once, regardless of channel conditions. Such data retransmission schemes and redundant transmission schemes are somewhat limited in that data is retransmitted even when it is undesirable or unnecessary to do so. Consequently, such IMDs may transmit extraneous telemetry signals, resulting in wasted transmitter output power and decreased IMD battery life.

BRIEF SUMMARY

An IMD as described herein can dynamically configure a data retransmission functionality to suit the particular contextual meaning of the data to be transmitted by the IMD. By reducing the amount of transmitted data in this manner, the IMD can conserve operating power and extend its battery life. An IMD as described herein may adjust a maximum number of retransmission attempts on a packet-by-packet basis according to the data type communicated between the IMD and the destination communication device.

The above and other aspects of the invention may be carried out in one embodiment by a method for operating an IMD. The method involves: obtaining contextual meaning information for data to be transmitted via telemetry communication from the IMD; adjusting a data retransmission configuration for the IMD in response to the contextual meaning information; and managing retransmission of the data to be transmitted, in accordance with the data retransmission configuration.

The above and other aspects of the invention may be carried out in another embodiment by a method for operating an IMD. The method involves: creating a data packet that contains data to be transmitted via telemetry communication from the IMD; associating a retransmission priority to the data packet, based upon contextual meaning information for the data to be transmitted; transmitting the data packet; and retransmitting the data packet as needed and in accordance with the retransmission priority.

The above and other aspects of the invention may be carried out in another embodiment by an IMD having: a data context module configured to process contextual meaning information for data to be transmitted by the IMD; a data retransmission module coupled to the data context module, the data retransmission module being configured to adjust a data retransmission configuration for the IMD in response to the contextual meaning information; and a transmitter coupled to the data retransmission module, the transmitter being controlled to manage retransmission of the data to be transmitted, in accordance with the data retransmission configuration.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
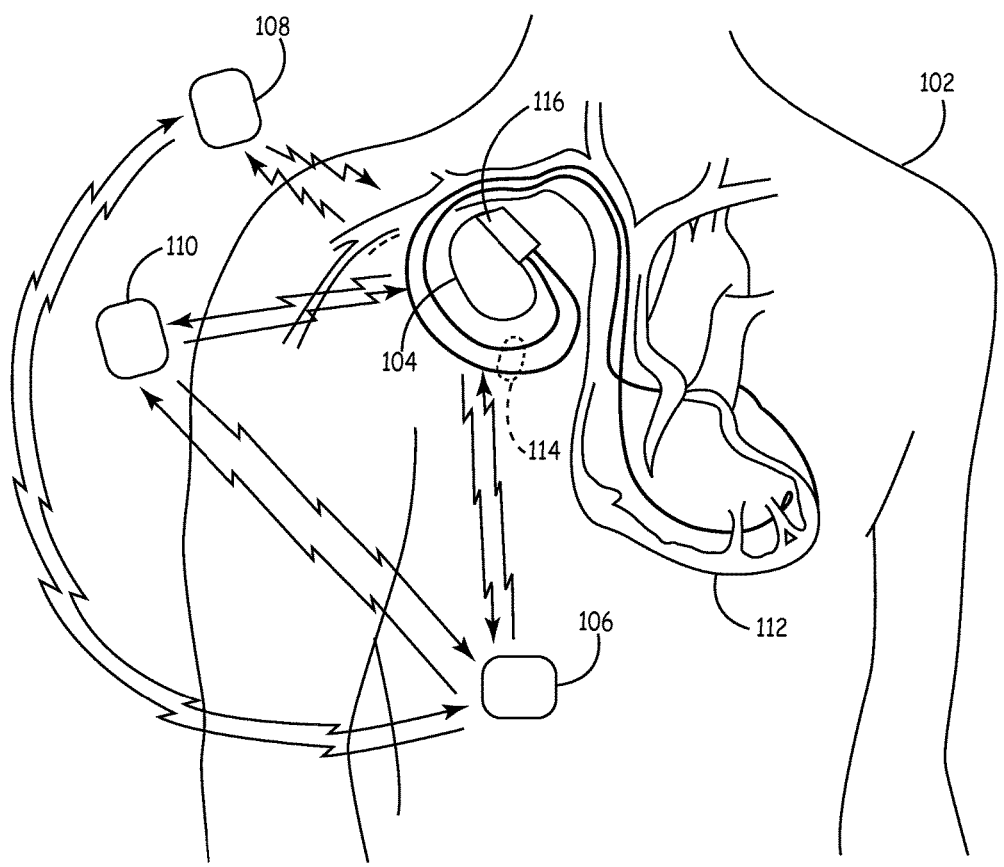
FIG. 1 is an illustration of a system including an IMD in accordance with certain embodiments of the invention.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the system described herein is merely one exemplary application for the invention.

For the sake of brevity, conventional techniques and features related to IMDs, IMD telemetry, signal processing, data transmission, signaling, IMD transceivers, and other functional aspects of the systems (and the individual operating components of the systems) are not described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

The following description refers to elements or features being "connected" or "coupled" together. As used herein, unless expressly stated otherwise, "connected" means that one element/feature is directly joined to (or directly communicates with) another element/feature, and not necessarily mechanically. Likewise, unless expressly stated otherwise, "coupled" means that one element/feature is directly or indirectly joined to (or directly or indirectly communicates with) another element/feature, and not necessarily mechanically. Thus, although the figures may depict example arrangements of elements, additional intervening elements, devices, features, or components may be present in an actual embodiment (assuming that the functionality of the device/system is not adversely affected).

The embodiments described herein can be implemented with any IMD having wireless telemetry capabilities. At present, a wide variety of IMDs are commercially available or proposed for clinical implantation. Such IMDs include pacemakers as well as ICDs, drug delivery pumps, cardiomyostimulators, cardiac and other physiologic monitors, nerve and muscle stimulators, deep brain stimulators, cochlear implants, and artificial organs (e.g., artificial hearts). In addition, as the technology advances, it is contemplated that IMDs shall become even more complex with respect to programmable operating modes, menus of operating parameters, and monitoring capabilities of increasing varieties of physiologic conditions and electrical signals. It is to be appreciated that embodiments of the present invention will be applicable in such emerging IMD technology as well. Further, the embodiments of the invention can be implemented in more than one IMD implanted within the same patient to enable telemetry communication between the IMDs.

FIG. 1 illustrates bi-directional telemetry communication involving one or more IMDs in accordance with certain embodiments. FIG. 1 generally represents a body area network system 100 having multiple devices configured to communicate with one another. As used herein, a "body area network" is a localized network of communicating devices associated with a single patient 102, where devices within the body area network are suitably configured to communicate with each other using one or more data communication protocols. A body area network device may be an IMD, a device affixed to the patient (such as a physiologic characteristic sensor or monitor), a device worn or held by the patient (such as a remote control device for an IMD, a wireless monitor device for an IMD, or a handheld programmer for an IMD), or a device in close proximity to the patient (such as an external programmer that communicates with an IMD). In this example, system 100 generally includes an IMD 104 implanted within patient 102, another IMD 106 implanted within patient 102, and two external communication devices 108/110 that are not implanted within patient 102.

In certain embodiments communications can take place between IMD 104 and any number of the devices within system 100. Moreover, telemetry communications may take place between devices (other than IMD 104) within system 100. The arrows in FIG. 1 represent such telemetry communications. In practice, a given communication session between two devices in system 100 may be unidirectional or bidirectional (in this example, FIG. 1 depicts bidirectional communications). In certain embodiments, the electrical devices can include one or more of at least one implantable medical instrumentation and of at least one external communication device. As shown in FIG. 1, in certain embodiments, the at least one implantable medical instrumentation can include IMD 104 and IMD 106, and the at least one external communication device can include external communication devices 108 and 110; however, it is to be appreciated that such quantities are not provided to limit the scope of application of embodiments of the invention.

In certain embodiments, when IMD 104 is used for cardiac applications (e.g., to provide cardiac sensing and pacing functions for patient 102), IMD 104 can be a cardiac device; for example, a pacemaker, an ICD, a hemodynamic monitor, or the like. As described above, however, neither IMD 104 nor any of the devices within system 100 should be limited to such applications or such devices. In this example, IMDs 104/106 are implanted in the same patient 102 beneath the patient's skin or muscle and, in certain embodiments, IMDs 104/106 can be typically oriented to the skin surface. In certain embodiments, when IMD 104 is used for cardiac applications, as shown, IMD 104 is electrically coupled to the heart 112 of the patient 102 through pace/sense or cardioversion/defibrillation electrodes operatively coupled to lead conductor(s) of one or more endocardial leads 114, which in turn, are coupled to a connector block 116 of IMD 104 in a manner well known in the art.

As generally mentioned above, among other design functions, each of the external communication devices 108/110 is designed for non-invasive communication with one or more of the IMDs 104/106, where such communication is enabled via downlink and uplink communication channels, which will be further described below. In certain embodiments, one or more of the external communication devices 108/110 can be an external pressure reference monitor ("EPR"). An EPR is typically used to derive reference pressure data for use in combination with absolute pressure derived from an IMD. In addition, an EPR measures and records barometric pressure which is necessary for correlation to atmospheric pressure. However, it is to be appreciated that embodiments of the invention are not limited to such EPR applications. Generally, any form of portable programmer, interrogator, recorder, monitor, or telemetered signals transmitter and/or receiver found suitable for communicating with IMD 104 and/or IMD 106, in turn, could be used for external communication devices 108/110.

Figure 2:
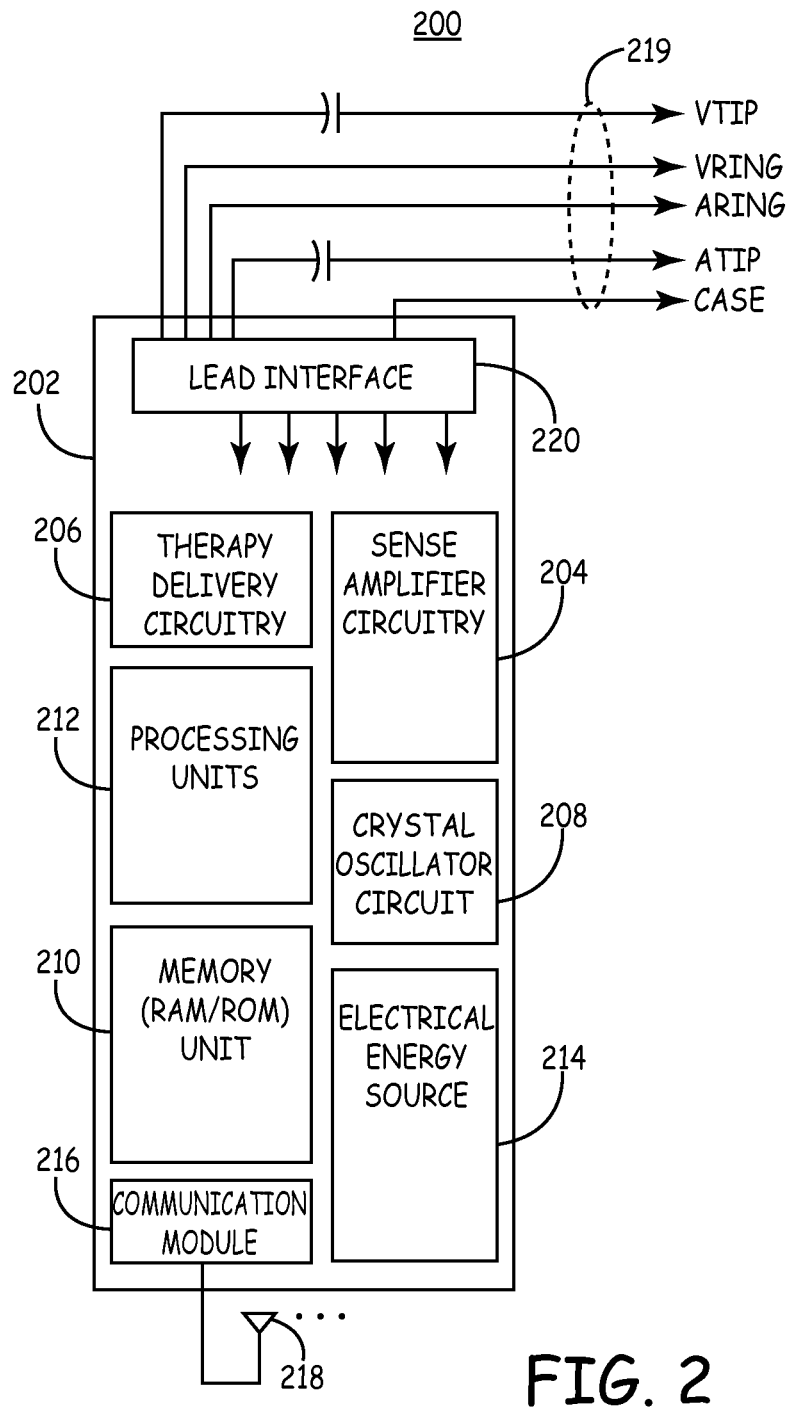
FIG. 2 is a block diagram of example circuitry of an IMD suitable for use in the system depicted in FIG. 1.

FIG. 2 shows an exemplary block diagram of the electronic circuitry of an IMD 200 configured in accordance with certain embodiments. IMD 104, IMD 106, and/or any other IMD implanted in patient 102 may be configured as shown in FIG. 2. As can be seen from FIG. 2, IMD 200 includes primary circuitry 202 for managing the operation and function of IMD 200, with such primary circuitry 202 being contained within a hermetic enclosure of IMD 200. The primary circuitry 202 includes a number of electrical components, most of which are exemplified in U.S. Pat. No. 6,539,253, entitled "Implantable Medical Device Incorporating Integrated Circuit Notch Filters" (incorporated herein by reference in relevant part). In certain embodiments, the primary circuitry 202 in FIG. 2 includes, without limitation: sense amplifier circuitry 204; therapy delivery circuitry 206; a crystal oscillator circuit 208; a suitable amount of memory 210, which may include random-access memory (RAM) and/or read-only memory (ROM); a processing unit 212; and an electrical energy source 214. In certain embodiments, the primary circuitry 202 also includes a communication module 216 and one or more antennas 219 configured to enable IMD 200 to communicate with other devices within and/or outside the body area network. It should be appreciated that the below descriptions of the primary circuitry 202 within the IMD 200 are merely example configurations.

In certain embodiments, when IMD 200 is used for cardiac applications (e.g., to provide cardiac sensing and pacing functions for the patient), the IMD 200 is coupled to the one or more endocardial leads 219 which, when implanted, extend transvenously between the implant site of the IMD 200 and the patient's heart, as previously noted with reference to FIG. 1. As mentioned above, the physical connections between the leads 219 and the various internal components of IMD 200 are facilitated by means of a conventional connector block assembly. Electrically, the coupling of the conductors of the leads 219 and internal electrical components of IMD 200 may be facilitated by means of a lead interface circuit 220 which functions, in a multiplexer-like manner, to selectively and dynamically establish necessary connections between various conductors in the leads 219 and individual electrical components of the IMD 200, as would be familiar to those of ordinary skill in the art. In certain embodiments, with respect to such cardiac applications, the various conductors in the leads 219 can include atrial tip and ring electrode conductors, ATIP and ARING, and ventricular tip and ring electrode conductors, VTIP and VRING. For the sake of clarity, the specific connections between the leads 219 and the various components of the IMD 200 are not shown in FIG. 2, although such connections will be familiar to those of ordinary skill in the art. For example, in cardiac applications, the leads 219 will necessarily be coupled, either directly or indirectly, to the sense amplifier circuitry 204 and the therapy delivery circuitry 206, in accordance with common practice, such that cardiac electrical signals may be conveyed to the sense amplifier circuitry 204 and such that stimulating pulses may be delivered by the therapy delivery circuitry 206 to cardiac tissue, via the leads 219. Also not shown in FIG. 2 is the protection circuitry commonly included in implanted devices to protect, for example, the sensing circuitry of the device from high voltage stimulating pulses.

As previously noted, the primary circuitry 202 includes the processing unit 212 which generally varies in sophistication and complexity depending upon the type and functional features of the IMD 200. In certain embodiments, the processing unit 212 can be an off-the-shelf programmable microprocessor, a microcontroller, a custom integrated circuit, or any of a wide variety of other implementations generally known. Although specific connections between the processing unit 212 and other components of the IMD 200 are not shown in FIG. 2, it will be apparent to those of ordinary skill in the art that the processing unit 212 functions to control the timed operation of the sense amplifier circuitry 204 and the therapy delivery circuitry 206. In certain embodiments, the functioning of the processing unit 212 would be under control of firmware and programmed software algorithms stored in memory 210 (e.g., RAM, ROM, PROM and/or reprogrammable ROM) and are carried out using a processing unit of a typical microprocessor core architecture. In certain embodiments, the processing unit 212 can also include a watchdog circuit, a DMA controller, a lock mover/reader, a CRC calculator, and other specific logic circuitry coupled together by on-chip bus, address bus, and power, clock, and control signal lines in paths or trees in a manner well known in the art.

In certain embodiments, as is known in the art, the electrical energy source 214 powers the primary circuitry 202 and can also be used to power electromechanical devices, such as valves or pumps, of a substance delivery IMD, or to provide electrical stimulation energy of an ICD shock generator, cardiac pacing pulse generator, or other electrical stimulation generator. In certain embodiments, the electrical energy source 214 is a high energy density, low voltage battery coupled with a power supply circuit having power-on-reset ("POR") capability. The power supply circuit provides one or more low voltage power supply signals, the POR signal, one or more voltage reference sources, current sources, an elective replacement indicator ("ERI") signal, and, in the case of an ICD, high voltage power to the therapy delivery circuitry 206. For the sake of clarity in the example block diagram provided in FIG. 2, the connections between the electrical energy source 214 and the electrical components of the IMD 200 are not shown, as one skilled in the art would be familiar with such connections.

In certain embodiments, the sense amplifier circuitry 204 can be configured to process physiologic signals that are used to trigger or modulate therapy delivery and are stored as physiologic signal data for later retrieval as described herein. Generally, the sense amplifier circuitry 204 is coupled to electrical signal sense electrodes and/or physiologic sensors on or in the housing of the IMD 200 or as mentioned above, situated at sites distanced from the IMD housing, typically in distal portions of the elongated leads 219. As is generally known, the sensors or electrodes located outside the housing are coupled by conductors to feedthrough pins of feedthroughs extending through the housing wall. Certain physiologic sensors or sense electrodes can be mounted to a connector assembly so that the conductors are quite short.

In certain embodiments, the conductors include the elongated conductors of the leads 219 extending to the remotely situated physiologic sensors and sense electrodes. As such, in some cardiac applications, the sense amplifier circuitry 204 is designed to receive electrical cardiac signals from the leads 219 and to process such signals to derive event signals reflecting the occurrence of specific cardiac electrical events, including atrial contractions (P-waves) and ventricular contractions (R-waves). These event-indicating signals are provided to the processing unit 212 for use in controlling the synchronous stimulating operations of the IMD 200 in accordance with common practice in the art. In addition, these event indicating signals may be communicated, via uplink transmission, to one or more external communication devices.

In example embodiments, the therapy delivery circuitry 206 can be configured to deliver electrical stimulation to the patient, e.g., cardioversion/defibrillation therapy pulses and/or cardiac pacing pulses delivered to the heart, or other electrical stimulation delivered to the brain, other organs, selected nerves, the spinal column, the cochlea, or muscle groups, including skeletal muscle wrapped about the heart. Alternatively, in certain embodiments, the therapy delivery circuitry 206 can be configured as a drug pump delivering drugs into organs for therapeutic treatment or into the spinal column for pain relief. Alternatively, in certain embodiments, the therapy delivery circuitry 206 can be configured to operate an implantable heart assist device or pump implanted in patients awaiting a heart transplant operation.

When the IMD 200 is used for cardiac applications, the sense amplifier circuitry 204 may also include patient activity sensors or other physiologic sensors for sensing the need for cardiac output and modulating pacing parameters accordingly through many alternative approaches set forth in the prior art. If the IMD 200 is an ICD, the therapy delivery circuitry 206 generally includes one or more high power cardioversion/defibrillation output capacitors, electronic circuitry coupled to the sense amplifiers for detecting and discriminating pathologic and/or nonpathologic arrhythmias from one another and providing other functions, high voltage electronic circuitry for charging the output capacitor(s) from a battery voltage to a higher voltage, and electronic switching circuitry for dumping the charge built up on the output capacitor(s) through the cardioversion/defibrillation electrodes operatively coupled to the one or more endocardial leads 219. Such IMDs are described in detail in U.S. Pat. Nos. 5,626,620 and 5,931,857.

Registers of the memory 210 can be used for storing data compiled from sensed cardiac activity and/or relating to device operating history or sensed physiologic parameters. Generally, the data storage can be triggered manually by the patient, on a periodic basis, or by detection logic (e.g., within the sense amplifier circuitry 204) upon satisfaction of certain programmed-in event detection criteria. If not manually triggered, in certain embodiments, the criteria for triggering data storage within the IMD 200 is programmed via telemetry transmitted instructions and parameter values. If manually triggered, in some cases, the IMD 200 includes a magnetic field sensitive switch (this may be a Hall effect sensor, or another received communications signal) that closes in response to a magnetic field, and the closure causes a magnetic switch circuit to issue a switch closed ("SC") signal to the processing unit 212 which responds in a "magnet mode." For example, the patient may be provided with a magnet (e.g., incorporated into an external communication device) that can be applied over the IMD 200 to close the switch and prompt the processing unit 212 to store physiologic episode data when the patient experiences certain symptoms and/or deliver a therapy to the patient. Following such triggering, in certain embodiments, event related data, e.g., the date and time, may be stored along with the stored periodically collected or patient initiated physiologic data. Typically, once stored, the data is ready for telemetry transmission on receipt of a retrieval or interrogation instruction.

Memory 210 may also be used to store data necessary to support the data retransmission adjustment procedures described herein. For example, memory 210 may be configured to store contextual meaning information related to data to be transmitted, data type categories, retransmission configuration settings, and/or other items that are processed or handled by IMD 200.

In certain embodiments, the crystal oscillator circuit 208 generally employs clocked CMOS digital logic ICs having a clock signal provided by a crystal (e.g., piezoelectric) and a system clock coupled thereto as well as discrete components, e.g., inductors, capacitors, transformers, high voltage protection diodes, and the like that are mounted with the ICs to one or more substrate or printed circuit board. Typically, each clock signal generated by the system clock is routed to all applicable clocked logic via a clock tree. In certain embodiments, the system clock provides one or more fixed frequency clock signals that are independent of the battery voltage over an operating battery voltage range for system timing and control functions and in formatting telemetry signal transmissions. Again, the lines over which such clocking signals are provided to the various timed components of the IMD 200 (e.g., processing unit 212) are omitted from FIG. 2 for the sake of clarity.

Those of ordinary skill in the art will appreciate that IMD 200 may include numerous other components and subsystems, for example, activity sensors and associated circuitry. The presence or absence of such additional components in IMD 200, however, is not believed to be pertinent to the present invention, which relates to the implementation and operation of a communication subsystem in the IMD 200, and associated communication subsystems in one or more of further implantable medical instrumentation and other electrical devices, such as external communication devices.

In certain embodiments, the IMD 200 can involve an implantable cardiac monitor without therapy delivery system 206, e.g., an implantable EGM monitor for recording the cardiac electrogram from electrodes remote from the heart as disclosed in U.S. Pat. No. 5,331,966. Alternatively, the IMD 200 can involve an implantable hemodynamic monitor ("IHM") for recording cardiac electrogram and other physiologic sensor derived signals, e.g., one or more of blood pressure, blood gases, temperature, electrical impedance of the heart and/or chest, and patient activity. The MEDRONIC® REVEAL® insertable loop recorder, having EGM electrodes spaced across its housing, is an example of the former, and the MEDRONIC® CHRONICLE® IHM, coupled with a capacitive pressure and temperature sensing lead and EGM sense electrodes of the type described in U.S. Pat. No. 5,564,434 is an example of the latter.

As described above, the IMD 200 includes communication module 216 and one or more antennas 218. Communication module 216 may include any number of transmitters, any number of receivers, and/or any number of transceivers, depending upon the particular implementation. As described in more detail below, IMD 200 may include configurable data retransmission logic, which may be realized in or executed by communication module 216, processing unit 212, memory unit 210, and/or elsewhere in IMD 200. In certain embodiments, each of the antennas 218 is mounted to the IMD 200 in one or more of a wide variety of configurations. For example, one or more of the antennas 218 can take the form of a surface mounted antenna (e.g., as described in U.S. Pat. No. 4,401,119, or one or more of the antennas 218 can be enclosed within or mounted to the IMD connector block assembly. However, it is to be appreciated that the invention should not be limited to such.

It is desirable to reduce the size of the IMD 200 while increasing its functional capabilities and prolonging battery life to increase longevity. In this regard, IMD 200 may be suitably configured to adjust its data retransmission characteristics and configuration as needed in response to information related to the context of the telemetry data. For example, the maximum number of retransmission attempts performed by IMD 200 may be adjusted upwardly or downwardly according to the type and/or the priority of the data to be transmitted. Moreover, the retransmit capability of IMD 200 may be disabled for certain types of data.

By way of background, the IMD telemetry system and functions are described as follows. For convenience of description, the embodiments described as follows use short range RF downlink telemetry transmissions and uplink telemetry transmissions, but it should be appreciated that the embodiments of the invention should not be limited to such. Similarly, the terms "telemeter," "telemetry transmission," and the like are intended to embrace any such action and manner of communicating and conveying data and commands between the IMD 200 and other electrical devices (e.g., other IMDs implanted within the same patient, external communication devices carried or worn by the patient, and/or external monitoring devices) in the uplink transmission direction and the downlink transmission direction.

In the IMD 200, uplink and downlink telemetry capabilities are provided to enable communication with other devices. IMD 200 may be configured to communicate in a conventional manner with one or more external electrical devices, a telemetry communication device, a more proximal medical device on the patient's body, or other implantable medical instrumentation in the patient's body. Generally, the stored physiologic data as well as one or more of real-time generated physiologic data and non-physiologic data (collectively referred to herein as "patient data") can be transmitted by uplink RF telemetry from the IMD 200 to the other devices or instrumentation in response to a downlink telemetered interrogation command, events within the IMD 200 or the patient, magnet swipe across the IMD 200 by the patient, upon satisfaction of certain programmed-in event detection criteria and/or timed events. The real-time physiologic data can include real time sampled signal levels, e.g., intracardiac electrocardiogram amplitude values, and sensor output signals. The non-physiologic patient data can include currently programmed device operating modes and parameter values, battery condition, device ID, patient ID, implantation dates, device programming history, real time event markers, and the like. In the context of implantable pacemakers and ICDs, such patient data can include programmed sense amplifier sensitivity, pacing or cardioversion pulse amplitude, energy, and pulse width, pacing or cardioversion lead impedance, programmed setting, and/or accumulated statistics related to device performance, e.g., data related to detected arrhythmia episodes and applied therapies.

Figure 3:
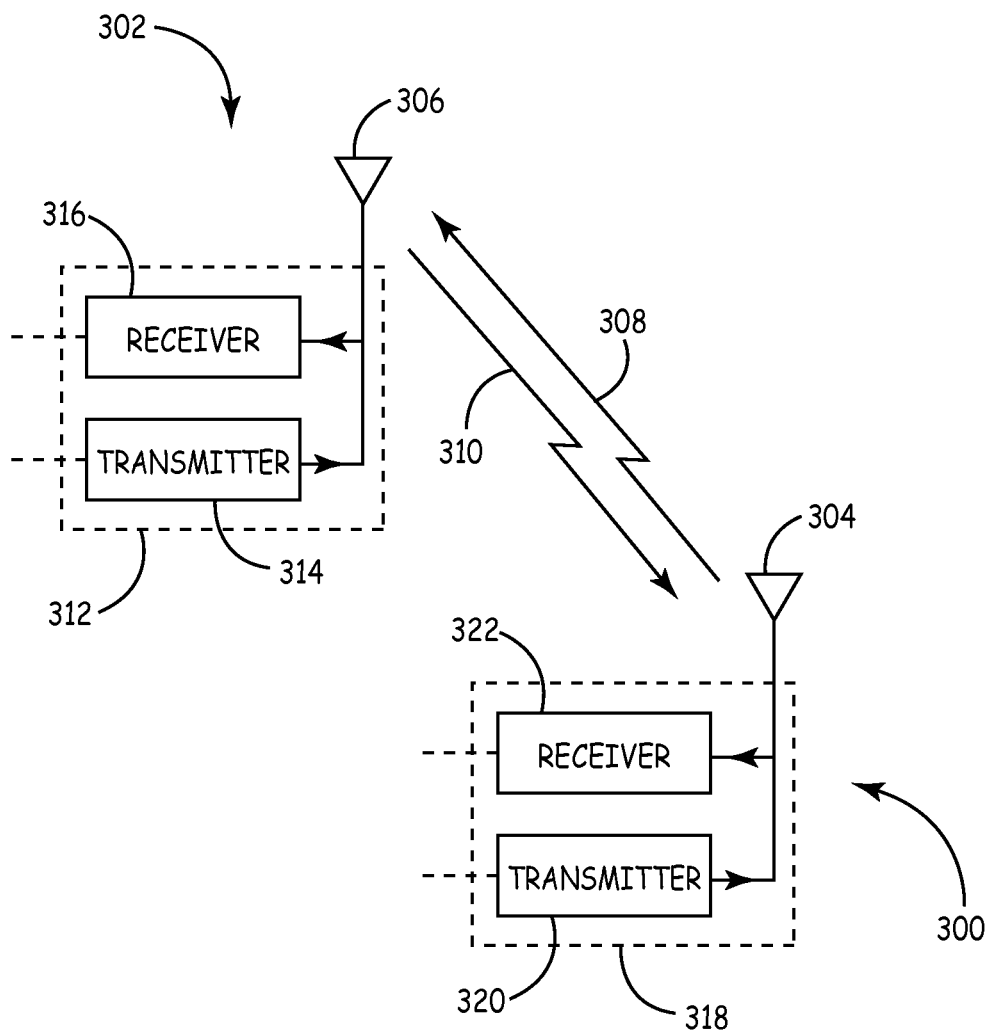
FIG. 3 is a block diagram depicting example communication modules suitable for use in an IMD communication system.

FIG. 3 depicts data communication between an IMD 300 and another device 302, which may be a device within the same body area network or any telemetry communication device. In certain embodiments, programming commands or patient data can be transmitted between one or more IMD antennas 304 associated with the IMD 300 and one or more antennas 306 associated with the device 302. In certain embodiments, a high frequency signal (or UHF, or VHF signal) can be employed. As such, it would not be necessary for antenna 306 to be held in close proximity to IMD 300. In other words, the system shown in FIG. 3 may be configured to support far field telemetry. For example, an external communication device 302 and an external communication device antenna 306 may be on a stand a few meters or so away from the patient. Moreover, the patient may be active and could be exercising on a treadmill or the like during a telemetry interrogation and transmission of real time ECG or physiologic parameters. An external communication device 302 may also be designed to universally program existing IMDs that employ the conventional ferrite core, wire coil, RF telemetry antenna of the prior art and therefore also have a conventional external communication device RF head and associated software for selective use with such IMDs.

In an uplink telemetry transmission 308, the antenna 306 operates as a telemetry receiver antenna, and the antenna 304 operates as a telemetry transmitter antenna. Conversely, in a downlink telemetry transmission 310, the antenna 306 operates as a telemetry transmitter antenna, and the antenna 304 operates as a telemetry receiver antenna. As shown with respect to FIG. 1, such telemetry transmissions may also be supported between two IMDs implanted within the same patient.

In certain embodiments, antenna 306 is electrically coupled to a telemetry transceiver or radio 312, which may include a telemetry transmitter 314 and a telemetry receiver 316. Similarly, in certain embodiments, antenna 304 is coupled to a telemetry transceiver or radio 318, which may include a telemetry transmitter 320 and a telemetry receiver 322. Referring to FIG. 2, telemetry transceiver 318 may be included within communications module 216 of the IMD 200. Alternatively, telemetry transceiver 318 may be coupled to communications module 216 to enable IMD operation as described herein. In certain embodiments, the telemetry transmitter and telemetry receiver of a given device can be coupled to control circuitry and registers under the control of a microcomputer and software maintained by the device.

In practice, the telemetered data can be encoded in any of a wide variety of telemetry formats. While not being limited to such, some examples of particular data encoding or modulation types and/or techniques that can be utilized with such data transmissions include noise modulation, general spread spectrum encoding, bi-phase encoding, quadrature phase shift keying, frequency shift keying ("FSK"), time division multiple access ("TDMA"), frequency division multiple access ("FDMA"), pre-emphasis/de-emphasis of baseband, vestigial, code division multiple access ("CDMA"), quadrature amplitude modulation ("QAM"), pi/8, quad-QAM, 256-QAM, 16-QAM, delta modulation, phase shift keying ("PSK"), quadrature phase shift keying ("QPSK"), quadrature amplitude shift keying ("QASK"), minimum shift keying, tamed frequency modulation ("TFM"), orthogonal frequency division multiplexing ("OFDM"), Bluetooth, any 802.11 modulation configuration, worldwide interoperability for microwave access ("Wi-MAX"), any 802.16 modulation configuration, 802.15.4, and Zigbee. Note that the "mode" used by the transceivers may be selected to optimize performance based on implant depth input and QoS input.

Depending upon the implementation of system, the telemetered data can be arranged for transmission (and reception) in any suitable manner. In practice, an IMD can be configured to transmit data organized as, without limitation: data packets; data frames; datagrams; data blocks; or any identifiable grouping. In certain embodiments, the uplink and downlink telemetry transmissions 308/310 between the IMD 300 and the device 302 follow a telemetry protocol that formulates, transmits, and demodulates data packets each comprising a bit stream of modulated data bits. In certain embodiments, the data packets are formulated of a data bit stream with a preamble, data and error checking data bits.

Figure 4:
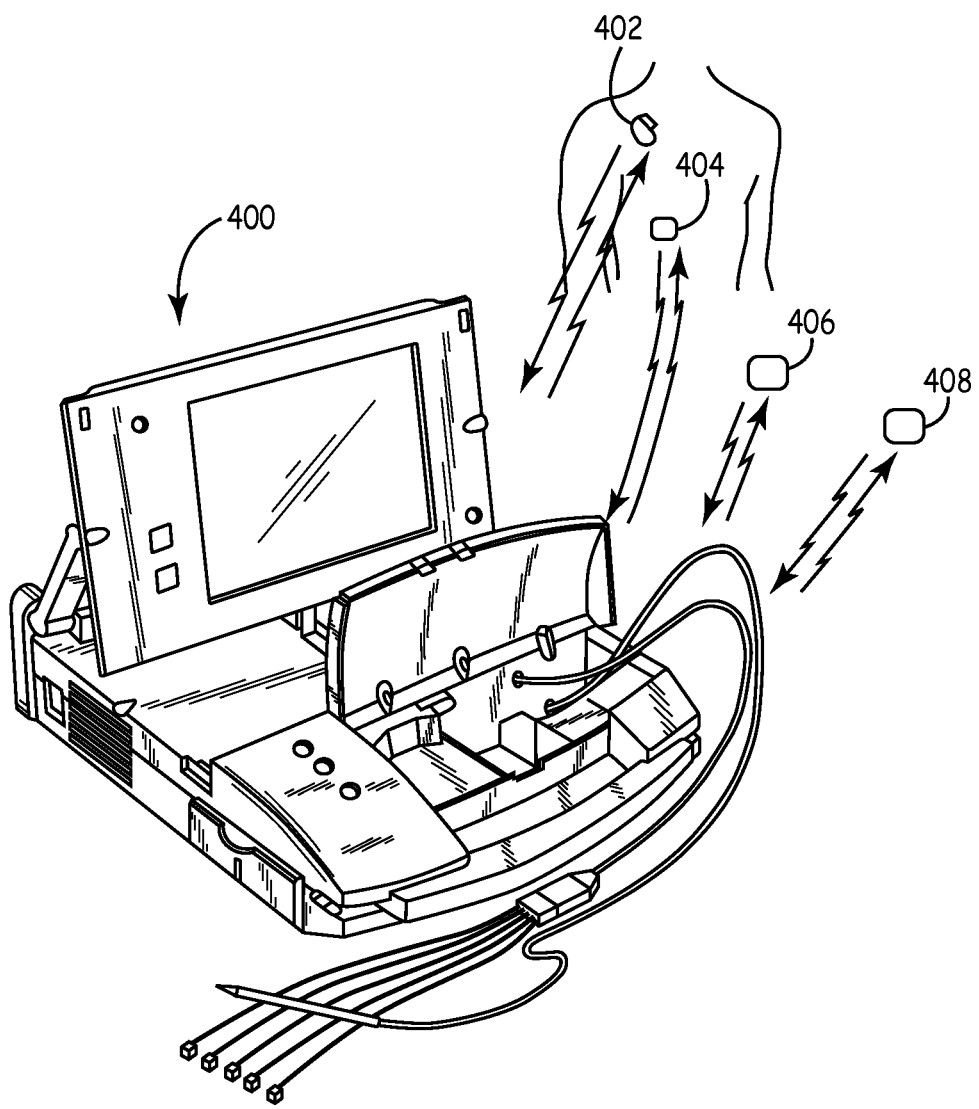
FIG. 4 is a perspective view of an external telemetry communication device configured to communicate with an IMD in accordance with certain embodiments of the invention.

In FIG. 4, there is shown a perspective view of an external device 400 configured in accordance with certain embodiments of the invention. In certain embodiments, the external device 400 can be used for telemetry communication with any number of IMDs 402/404 and/or any number of external communication devices 406/408. From such telemetry communications, the external device 400 can be subsequently used to display or further transmit patient data. The external device 400 generally includes a processing unit (not visibly shown). As should be appreciated, the processing unit can include any of a wide variety of devices. While not being limited to such, the processing unit, in certain embodiments, can be a personal computer type motherboard, e.g., a computer motherboard including a microprocessor and related circuitry such as digital memory. The details of design and operation of the computer system will not be set forth in detail in the present disclosure, as it is believed that such details are well-known to those of ordinary skill in the art. However, such external processing monitors are described in more detail in U.S. Pat. Nos. 5,345,362 and 5,683,432, which are incorporated herein by reference in their relevant parts. While not shown, it is to be appreciated that such telemetry communications between the external device 400 and the devices within the body area network (e.g., IMDs 402/404 and external communication devices 406/408) can occur in combination with telemetry communications occurring between IMDs 402/404, between external communication devices 406/408, and/or between one or more of the IMDs 402/404 and one or more of the external communication devices 406/408 (as exemplified in FIG. 1).

As described in more detail below, external device 400 may be suitably configured to function as an IMD programming device that provides data, programming instructions, and other information to an IMD that supports the dynamic retransmission features described herein. In one embodiment, external device 400 is configured to generate an acknowledgment ("ACK") message when it successfully receives data from an IMD. External device 400 may also be configured to generate a negative acknowledgment ("NAK") message when data is received with errors or is otherwise corrupted. In response to a NAK message, an IMD may attempt to retransmit previously transmitted data.

Figure 5:
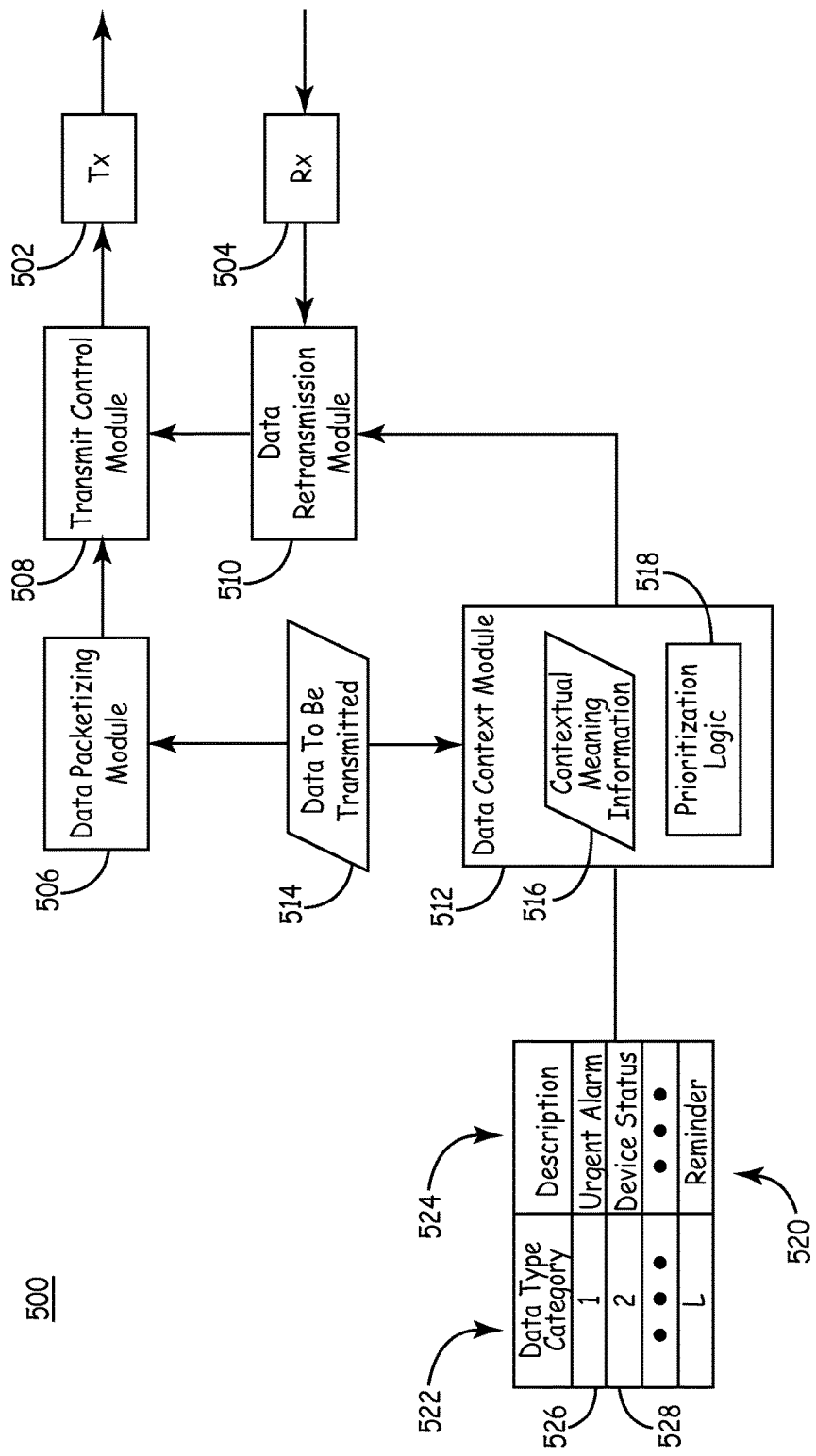
FIG. 5 is a schematic representation of a portion of an example IMD that supports dynamic data retransmission in accordance with example embodiments of the invention.

FIG. 5 is a schematic representation of a portion of an example IMD 500 that supports the dynamic data retransmission feature described herein. It should be appreciated that FIG. 5 is a very simplified depiction of a portion of IMD 500, and that an embodiment of IMD 500 will include additional components and logic that support conventional operating aspects of IMD 500. For example, an embodiment of IMD 500 may include the components and logic described above with respect to FIG. 2. It should also be appreciated that an embodiment of an IMD need not support all of the data retransmission modes and features described herein, however, IMD 500 is depicted as a "full featured" version for convenience.

IMD 500 may include, without limitation: at least one transmitter 502, at least one receiver 504, a data packetizing module 506, a transmit control module 508, a data retransmission module 510, and a data context module 512. In practice, transmitter 502 and receiver 504 may be realized in one transceiver or radio module. Moreover, two or more of the functional blocks depicted in FIG. 5 may be combined into a single logical element. For example, data packetizing module 506, transmit control module 508, and data retransmission module 510 may be realized as one operating module. IMD 500 also includes an appropriate amount of memory for storing data maintained and/or processed by IMD 500 in the context of the data retransmission routines described herein. The various components, modules, and processing logic of IMD 500 may be coupled as needed using any suitable interconnection architecture. Referring to FIG. 2, transmitter 502 and receiver 504 may be implemented in communication module 216, while data packetizing module 506, transmit control module 508, data retransmission module 510, and data context module 512 (or respective portions thereof) may be implemented in processing units 212, memory unit 210, and/or communication module 216.

As described above, IMD 500 is suitably configured to transmit data to a destination device via telemetry communication. In this regard, FIG. 5 depicts data to be transmitted 514, which may be generated, stored, maintained, and formatted in any suitable manner. Data to be transmitted 514 may include, without limitation: control data for IMD 500; control data for the destination device; wakeup packet data for the destination device, which may include initialization data and operating instructions or requests for the destination device; overhead or signaling information associated with the communication channel between IMD 500 and the destination device; monitoring information related to the operation of IMD 500; patient status information; physiologic patient data; device activation instructions; programming signals; status information for IMD 500; time and date information; reminders; event markers; alarms or alerts; alarm/alert status information; notifications; and/or other information related to the operation, status, or condition of the patient, related to IMD 500, or related to the destination device.

This example assumes that IMD 500 transmits data in packets (or frames). Accordingly, IMD 500 may utilize data packetizing module 506 to packetize data to be transmitted 514. Data packetizing module 506 may utilize any suitable technique to create data packets that contain the appropriate amount of data to be transmitted 514 such that IMD 500 can process and send data to be transmitted 514 on a packet-by-packet basis. Transmit control module 508 may be realized as processing logic that manages the transmission and retransmission of data packets. Transmit control module 508 may, for example, regulate the timing of packet transmissions, regulate the timing of packet retransmissions, and control any adjustable characteristics of transmitter 502. In practice, transmit control module 508 can control transmitter 502 to manage retransmission of data to be transmitted 514, in accordance with a current data retransmission configuration of IMD 500.

The data retransmission configuration for IMD 500 relates to the manner in which IMD 500 handles the retransmission of data. The data retransmission configuration for IMD 500 can be modified or adjusted in realtime in accordance with the data to be transmitted 514. In one embodiment, the data retransmission configuration includes a setting for the maximum number of retransmission attempts for the IMD. This maximum number may be adjusted on a packet-by-packet basis, adjusted periodically after transmission of a designated number of packets, adjusted on a temporal basis, and/or adjusted on any appropriate basis. In other words, the frequency of these adjustments may vary depending upon the particular implementation of IMD 500. The maximum number of retransmission attempts may be set to zero, which effectively disables the data retransmission function of IMD 500 until the maximum number is changed to a number that is equal to or greater than one. The data retransmission configuration may also include a setting that influences a redundant transmission procedure for data transmitted by IMD 500. Some IMDs employ redundant transmission, where each data packet is retransmitted by default as a backup measure. IMD 500 may be configured to disable this redundant transmission feature as needed to conserve operating power. This feature of IMD 500 is described in more detail below.

Data context module 512 and data retransmission module 510 cooperate in a manner that allows IMD 500 to dynamically adjust its data retransmission scheme as needed. This feature can result in power savings and increased battery life by reducing the number of unnecessary data retransmissions. For this example, data context module 512 processes or analyzes data to be transmitted 514 (in particular, data context module 512 processes contextual meaning information 516 for data to be transmitted 514). In response to the contextual meaning information 516 associated with the data contained in a given packet, data retransmission module 510 adjusts a data retransmission (or "retry") configuration for IMD 500. The data retransmission configuration can be dynamically adjusted on a packet-by-packet basis, or in any suitable manner.

Depending upon the particular implementation, data retransmission module 510 may be configured to process contextual meaning information 516 in the manner described herein. Contextual meaning information 516 is information that is indicative of the type, purpose, or function of the data to be transmitted by IMD 500. In this embodiment, IMD 500 may utilize data context module 512 (or any equivalent processing logic) that determines, processes, or analyzes the context or meaning of the data to be transmitted 514 by IMD 500. Data context module 512 may be suitably configured to consider any number of factors that may influence contextual meaning information 516 and, in turn, influence the data retransmission characteristics of IMD 500. For example, data context module 512 may analyze signaling or overhead data contained in a data packet to be transmitted by IMD 500, where such signaling or overhead data identifies the type, operation, function, or purpose of the telemetry data contained in that packet.

In example embodiments, the contextual meaning information 516 may include, represent, or indicate a priority for the data to be transmitted, such that IMD 500 will utilize a more aggressive data retransmission configuration for relatively high priority data and a less aggressive data retransmission configuration for relatively low priority data. Indeed, IMD 500 may be controlled to prevent retransmission of data packets that contain certain types of data. IMD 500 may utilize prioritization logic 518 (or any equivalent processing logic), which can be configured to generate or analyze a priority for the data to be transmitted 514. Prioritization logic 518 may be designed to analyze signaling or overhead data contained in a data packet to be transmitted by IMD 500, where such signaling or overhead data identifies the type, operation, function, or purpose of the telemetry data contained in that packet. In turn, prioritization logic 518 may generate the priority for the data using any suitable procedure (e.g., a table lookup, an appropriate algorithm, or the like). As depicted in FIG. 5, the priority may be processed by data context module 512 such that contextual meaning information 516 is based at least in part upon the priority, or such that the contextual meaning information 516 otherwise indicates the priority.

In example embodiments, the contextual meaning information 516 may include, represent, or indicate a data type category for the data to be transmitted 514. One data type category may correspond to a first data retransmission setting or scheme, while another data type category may correspond to a second data retransmission setting or scheme. For example, a first data type category may correspond to telemetry data that ought to be transmitted in a redundant manner and with a setting that allows for a high number of retry attempts, a second data type category may correspond to telemetry data that ought to be transmitted with a setting that allows for a limited number of retry attempts (e.g., only one or two attempts), and a third data type category may correspond to telemetry data that ought to be transmitted only once regardless of transmission success. As depicted in FIG. 5, data context module 512 may process the data type category such that contextual meaning information 516 is based at least in part upon the data type category.

Data context module 512 and/or data retransmission module 510 may receive the data type category information in any appropriate manner. For example, IMD 500 may utilize a memory element 520 to store data type category information. Referring again to FIG. 2, memory element 520 may be realized in memory unit 210. Memory element 520, which is coupled to data context module 512 in this example, may be configured to store a list of data type categories 522 that identify the different categories of data handled by IMD 500. The ellipses in memory element 520 indicate that memory element 520 can store any number (L) of data type categories 522. Memory element 520 may also store descriptions 524 of the specific data or information that falls within the respective data type categories 522. In this example, a first data type category 526 includes urgent alarms; data type category 526 may also include other relatively urgent data items that are treated in a particular manner by IMD 500. In this example, a second data type category 528 includes device status information; data type category 528 may also include other relatively routine data items that are treated in a different manner by IMD 500. In practice, IMD 500 may increase its maximum number of retransmission attempts for data that falls in data type category 526, and decrease its maximum number of retransmission attempts for data that falls in data type category 528.

FIG. 5 depicts one example environment where contextual meaning information 516 is obtained locally at IMD 500, and where the data type category information is stored and obtained locally at IMD 500. Although not specifically shown in FIG. 5, receiver 504 may receive some contextual meaning information 516 and/or some data type category information in telemetry communications from an IMD programming device such that IMD 500 can process the received information in an appropriate manner and provide contextual meaning information 516 to data context module 512 and/or to data retransmission module 510. In alternate embodiments, IMD 500 may be configured to receive such information from a telemetry communication device, from another external source, via manipulation of a user interface of IMD 500, via a wireless and/or wired connection to a computing device (e.g., a personal computer, a laptop computer, a personal digital assistant, etc.), from a portable data storage device, or the like.

In the example embodiment, IMD 500 is able to process contextual meaning information 516 in a substantially real-time manner to provide dynamic adjustment of the IMD data retransmission characteristics. Thus, IMD 500 can dynamically adjust its operating parameters to conserve energy and extend battery life while maintaining telemetry communication links as needed for the current operating environment, the context of the telemetry data, and the like.

Data retransmission module 510 is suitably configured to adjust the data retransmission configuration for IMD 500 in response to contextual meaning information 516. In this example, data retransmission module 510 obtains contextual meaning information 516, and sets the maximum number of retransmission attempts for IMD 500. As described above, this setting determines whether IMD 500 will perform retransmissions for a given data packet and, if so, how many retry attempts will be performed for the given data packet.

Transmitter 502 is coupled to transmit control module 508. Transmitter 502 is configured to transmit telemetry signals from IMD 500, where such telemetry signals may be intended for any suitable device, system, or architecture (e.g., another IMD, an external programming device, a computing device, a telemetry communication device, a monitor, etc.). Transmitter 502 and IMD 500 may leverage known technologies to support telemetry communication according to accepted data transmission protocols, regulations, standards, or the like.

In the illustrated embodiment, receiver 504 is coupled to data retransmission module 510. Receiver 504 is configured to receive telemetry signals intended for IMD 500, where such telemetry signals may originate at any suitable device, system, or architecture (e.g., another IMD, an external programming device, a computing device, a telemetry communication device, a monitor, etc.). Receiver 504 and IMD 500 may leverage known technologies to support telemetry communication according to accepted data transmission protocols, regulations, standards, or the like. In this embodiment, receiver 504 is suitably configured to receive acknowledgement ("ACK") messages and negative acknowledgement ("NAK") messages associated with data transmitted from IMD 500. An ACK message may be generated and transmitted by the destination device upon successful receipt of data, while a NAK message may be generated and transmitted by the destination device upon receipt of corrupted data (e.g., data that does not pass an error check procedure), if the destination device receives real-time data (e.g., data having time sensitivity or time significance, such as event markers, or device operating status) out of sequence, and/or if the destination device fails to receive data within an expected period of time. IMD 500 can process ACK and NAK messages in connection with the data retransmission scheme described herein.

In alternate embodiments, some or all of the data retransmission processing intelligence may reside at an IMD programming device or any telemetry communication device that can link to IMD 500. For example, an IMD programming device may include a data context module described above. In such an embodiment, the IMD programming device may be configured to determine a suitable data retransmission configuration for IMD 500 and generate appropriate instructions for IMD 500. Upon receipt, IMD 500 can simply execute the instructions and configure its data retransmission scheme accordingly.

Figure 6:
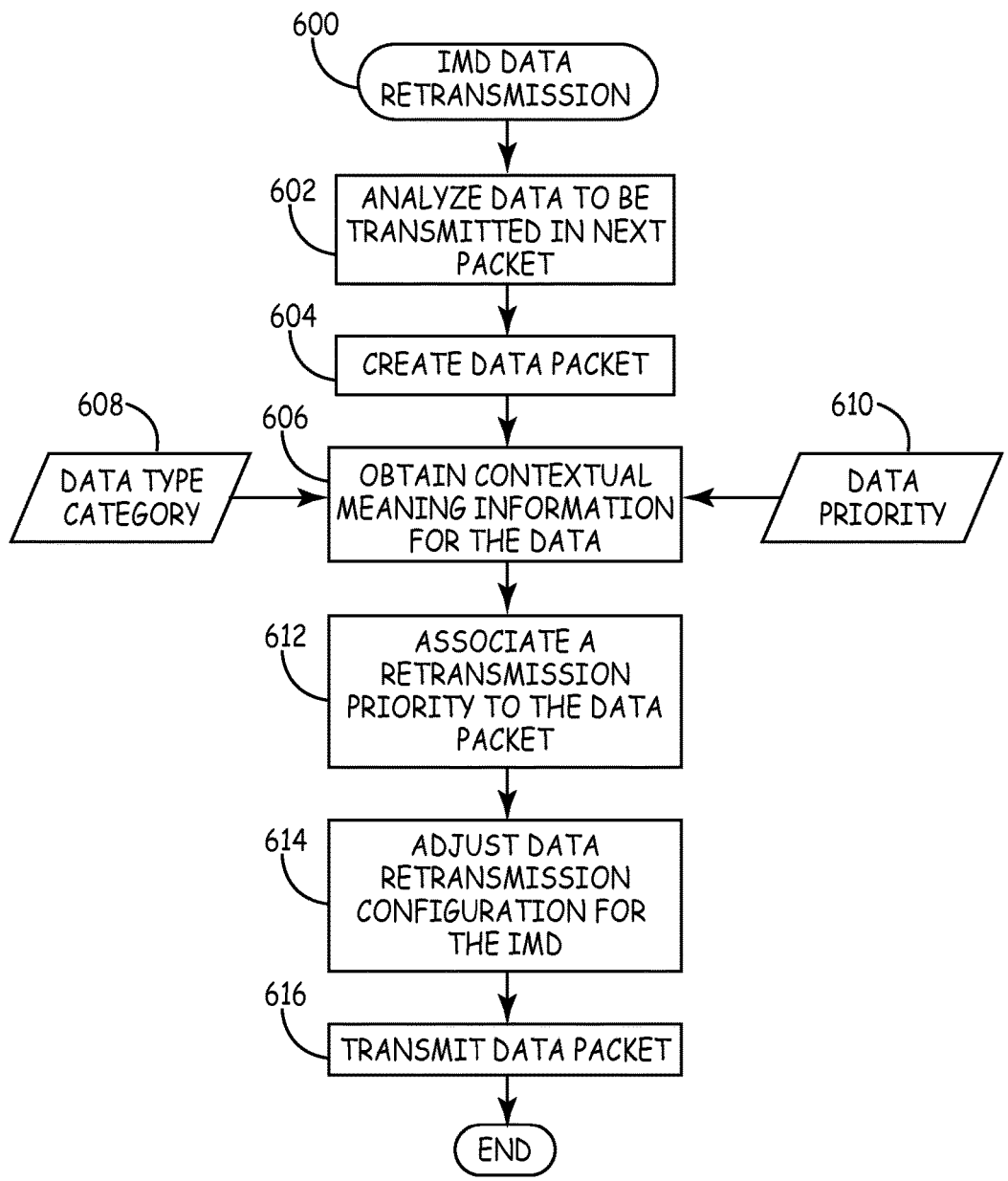
FIG. 6 is a flow chart illustrating an IMD data retransmission process.

FIG. 6 is a flow chart illustrating an IMD data retransmission process 600. Process 600 may be performed by any suitably configured IMD, such as IMD 500. The various tasks performed in connection with process 600 may be performed by software, hardware, firmware, or any combination thereof. For illustrative purposes, the following description of process 600 may refer to elements mentioned above in connection with FIGS. 1-5. In embodiments of the invention, portions of process 600 may be performed by different elements of the described system, e.g., one or more processing elements of IMD 500, transmitter 502, transmit control module 508, data retransmission module 510, or data context module 512. It should be appreciated that process 600 may include any number of additional or alternative tasks, the tasks shown in FIG. 6 need not be performed in the illustrated order, and process 600 may be incorporated into a more comprehensive procedure or process having additional functionality not described in detail herein.

Process 600 represents a packet-by-packet handling of data to be transmitted by an IMD (process 600 may be modified to handle data in a manner that is not packet-based). For this example, process 600 will analyze or otherwise process the data to be transmitted in the next packet (task 602), where this data represents the actual information to be sent to a destination device in contrast to overhead or signaling information that may also be included in a packet. Process 600 will create an appropriately formatted data packet that contains data to be transmitted via telemetry communication from the IMD (task 604). As a result of the analysis of the data (task 602), process 600 may obtain contextual meaning information for the data to be transmitted in the current data packet (task 606). As described previously, the contextual meaning information may include, be generated from, indicate, or be derived from a priority for the data to be transmitted and/or from a data type category for the data to be transmitted. FIG. 6 schematically depicts a data type category 608 and a data priority 610 as "inputs" to task 606 to illustrate how contextual meaning information may be obtained in a practical embodiment. Referring to FIG. 5, the IMD can maintain a list of data type categories in a memory element 520, where data type category 608 is included in the list.

The IMD processes the contextual meaning information and, if necessary, adjusts its dynamic data retransmission scheme in response to the contextual meaning information. In one embodiment, process 600 associates a retransmission priority to the current data packet (task 612), where the retransmission priority is based upon the contextual meaning information. For example, relatively important data (such as alarms, critical physiological patient data, or the like) can be assigned a high retransmission priority, while less important data (such as periodic device status data) can be assigned a low retransmission priority. The number of different priorities may vary from one IMD to another. Process 600 may utilize the retransmission priority and/or other configuration data to adjust the data retransmission configuration for the IMD (task 614). Thus, the data retransmission configuration for any given data packet can be based upon the priority of the data to be transmitted, the data type category of the data to be transmitted, and/or the retransmission priority.

In this example, the IMD adjusts its data retransmission configuration to set a maximum number of retransmission attempts for the data packet. Thus, task 614 may include the setting of the maximum number of retransmission attempts, where higher numbers are generally used for higher priority data and vice versa. Task 614 may set the maximum number to zero (or a number less than one) to effectively disable the data retransmission function of the IMD. In other words, task 614 may adjust the data retransmission configuration such that data packets are only transmitted once. Eventually, process 600 transmits the data packet (task 616) to the intended destination device in accordance with the given data transmission protocol, modulation scheme, etc.

Figure 7:
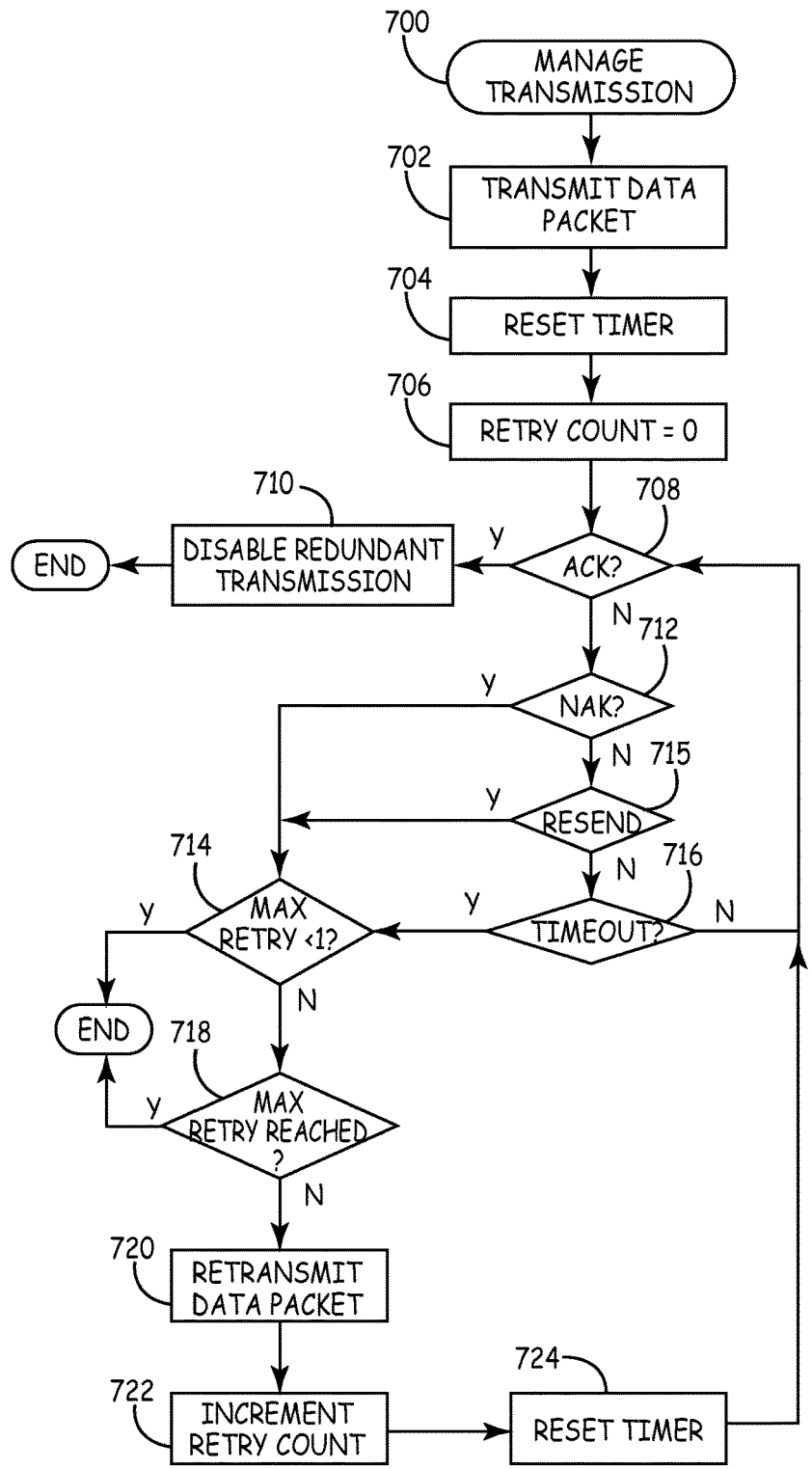
FIG. 7 is a flow chart illustrating a manage retransmission process.

FIG. 7 is a flow chart illustrating a manage retransmission process 700. Process 700 may be performed by any suitably configured IMD, such as IMD 500. The various tasks performed in connection with process 700 may be performed by software, hardware, firmware, or any combination thereof. For illustrative purposes, the following description of process 700 may refer to elements mentioned above in connection with FIGS. 1-5. In embodiments of the invention, portions of process 700 may be performed by different elements of the described system, e.g., one or more processing elements of IMD 500, transmitter 502, receiver 504, transmit control module 508, data retransmission module 510, or data context module 512. It should be appreciated that process 700 may include any number of additional or alternative tasks, the tasks shown in FIG. 7 need not be performed in the illustrated order, and process 700 may be incorporated into a more comprehensive procedure or process having additional functionality not described in detail herein. Moreover, even though process 600 and process 700 are depicted separately, the two may be realized in a combined fashion.

Process 700 is performed by an IMD to manage retransmission of data to be transmitted in accordance with a designated data retransmission configuration, which may have a setting that indicates the maximum number of retry attempts for data packets transmitted by the IMD. The IMD transmits a data packet to a destination device (task 702), and the IMD may reset an appropriate timer or counter (task 704) corresponding to the transmitted data packet. Depending upon the implementation, the timer/counter may accumulate time, count outgoing data packets, or the like, for purposes of determining whether to attempt a retransmission of the current data packet. In addition to the resetting of the timer/counter, process 700 may clear or zero the retry count for the current data packet (task 706), which indicates that retransmission of the current data packet has not been attempted yet.

If the IMD receives an ACK (query task 708) before the timer/counter expires, then process 700 may proceed to a task 710. In this situation, the ACK represents a "successful transmission" indication for the quantity of data previously transmitted in the data packet (task 702). Some IMDs perform a redundant transmission procedure such that all data packets are retransmitted at least once by default. For such IMDs, task 710 can be performed to disable the redundant transmission procedure for the current data packet, thus conserving IMD operating power by preventing unnecessary retries. Following task 710, process 700 ends (or it may be reentered at task 702 to transmit another data packet).

If the IMD receives a NAK (query task 712) before the timer/counter expires, then process 700 may proceed to a query task 714. Query task 714 may also be entered if the IMD receives a resend request (query task 715) from the destination device; a resend request may be generated if, for example, the destination device receives real-time data out of sequence. Query task 714 may also be entered if the timer/counter expires or times out (query task 716) before the IMD receives an ACK or a NAK. In this example, query task 714 checks whether the maximum number of retry attempts is less than one (e.g., zero). If so, then process 700 ends, or is reentered at task 702, without retransmitting the current data packet. In other words, if the maximum number of retry attempts is zero, then the data retransmission configuration of the IMD will prevent retransmission of the current data packet.

If the maximum number of retry attempts is at least one, then process 700 may check whether the maximum number of retry attempts has been reached (query task 718). If so, then process 700 ends, or is reentered at task 702. If the maximum number of retry attempts has not been reached (query task 718), then the IMD is controlled to retransmit the current data packet (task 720). In response to this retransmission, process 700 increments the retry count (task 722) and resets the timer/counter as appropriate (task 724). In practice, the timer/counter may correspond to a longer period for the initial transmission and a shorter period for subsequent retransmissions. Following task 724, process 700 may be reentered at query task 708 to again monitor for an ACK or a NAK message. In this manner, process 700 manages retransmission of data packets as needed and in accordance with the designated data retransmission configuration of the IMD.

An IMD can utilize the techniques and technologies described herein to prioritize uplink data packets and to activate, deactivate, and/or dynamically adjust its data retransmission capability. Under poor channel conditions, relatively important (high priority) data will be retransmitted, while less important data may be discarded without retransmission, thus conserving power. Less important data may include routine real-time status information that is updated frequently and which therefore becomes stale and unnecessary if not received immediately by the destination device. Moreover, if data is successfully transmitted the first time, the IMD can disable its default redundant transmission feature (if applicable) to save transmit power. Otherwise, some data may be unnecessarily transmitted multiple times.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention, where the scope of the invention is defined by the claims, which includes known equivalents and foreseeable equivalents at the time of filing this patent application.

The invention claimed is:

1. A method for operating an implantable medical device ("IMD"), the method comprising:
   obtaining contextual meaning information for data to be transmitted via telemetry communication from the IMD;
   adjusting a data retransmission configuration for the IMD in response to the contextual meaning information;
   transmitting the data to be transmitted from the IMD via telemetry communication; and
   managing retransmission, by the IMD, of the previously transmitted data from the IMD via telemetry communication in accordance with the data retransmission configuration.

2. A method according to claim 1, wherein:
   the contextual meaning information indicates a data type category for the data to be transmitted; and
   the data retransmission configuration is based upon the data type category.

3. A method according to claim 2, further comprising maintaining a list of data type categories for the IMD, the data type category being included in the list.

4. A method according to claim 1, further comprising generating a priority for the data to be transmitted, wherein:
   the contextual meaning information indicates the priority; and
   the data retransmission configuration is based upon the priority.

5. A method according to claim 1, wherein adjusting the data retransmission configuration comprises setting a maximum number of retransmission attempts for the IMD.

6. A method according to claim 1, wherein adjusting the data retransmission configuration comprises disabling a data retransmission function of the IMD.

7. A method according to claim 1, wherein the IMD performs a redundant transmission procedure for data transmitted via telemetry communication from the IMD, and the method further comprises:
   receiving a successful transmission indication for a quantity of data previously transmitted via telemetry communication from the IMD; and
   disabling, in response to the successful transmission indication, the redundant transmission procedure for the quantity of data.

8. The method of claim 1, wherein transmitting the data from the IMD comprises transmitting the data from the IMD via wireless telemetry communication.

9. An implantable medical device ("IMD") comprising:
   a data context module configured to process contextual meaning information for data to be transmitted by the IMD;
   a data retransmission module coupled to the data context module, the data retransmission module being configured to adjust a data retransmission configuration for the IMD in response to the contextual meaning information; and
   a transmitter coupled to the data retransmission module, the transmitter being controlled to transmit the data to be transmitted from the IMD via telemetry communication and manage retransmission, by the IMD, of the previously transmitted data from the IMD via telemetry communication in accordance with the data retransmission configuration.

10. An IMD according to claim 9, wherein:
    the contextual meaning information indicates a data type category for the data to be transmitted; and
    the data retransmission configuration is based upon the data type category.

11. An IMD according to claim 10, further comprising memory coupled to the data context module, and configured to store a list of data type categories for the IMD, the data type category being included in the list.

12. An IMD according to claim 9, further comprising prioritization logic coupled to the data context module, and configured to generate a priority for the data to be transmitted, wherein:
    the contextual meaning information indicates the priority; and
    the data retransmission configuration is based upon the priority.

13. An IMD according to claim 9, wherein the data retransmission module is configured to adjust the data retransmission configuration by setting a maximum number of retransmission attempts for the IMD.

14. An IMD according to claim 9, wherein the data retransmission module is configured to adjust the data retransmission configuration by disabling a data retransmission function of the IMD.

15. The IMD of claim 9, wherein the transmitter is configured to transmit the data from the IMD via wireless telemetry communication.

16. A method for operating an implantable medical device ("IMD"), the method comprising:
    creating a data packet that contains data to be transmitted via telemetry communication from the IMD;
    associating a retransmission priority to the data packet, based upon contextual meaning information for the data to be transmitted;
    transmitting the data packet from the IMD via telemetry communication; and
    retransmitting, with the IMD, the data packet previously transmitted from the IMD via telemetry communication as needed and in accordance with the retransmission priority.

17. A method according to claim 16, further comprising setting a maximum number of retransmission attempts for the data packet, the maximum number being influenced by the retransmission priority.

18. A method according to claim 17, further comprising preventing retransmission of the data packet if the maximum number is less than one.

19. A method according to claim 16, further comprising obtaining the contextual meaning information for the data to be transmitted.

20. A method according to claim 16, further comprising adjusting a data retransmission configuration for the IMD in response to the retransmission priority.

21. A method according to claim 16, wherein the contextual meaning information indicates a data type category for the data to be transmitted.

22. A method according to claim 16, wherein the IMD performs a redundant transmission procedure for data transmitted via telemetry communication from the IMD, and the method further comprises:
  receiving a successful transmission indication for the data packet; and
  disabling, in response to the successful transmission indication, the redundant transmission procedure for the data packet.

* * * * *